US012788474B2

(12) United States Patent
Britva et al.

(10) Patent No.: US 12,788,474 B2
(45) Date of Patent: Nov. 10, 2026

(54) SYSTEM AND METHOD FOR HEATING BIOLOGICAL TISSUE

(71) Applicant: Alma Lasers Ltd., Caesarea (IL)

(72) Inventors: Alexander Britva, Migdal Ha'Emek (IL); Alexander Dverin, Netanya (IL); Alexander Belozertsev, Petah Tikva (IL)

(73) Assignee: Alma Lasers LTD., Caesarea (IL)

( * ) Notice: Subject to any disclaimer, the term of this patent is extended or adjusted under 35 U.S.C. 154(b) by 143 days.

(21) Appl. No.: 18/429,606

(22) Filed: Feb. 1, 2024

(65) Prior Publication Data

US 2024/0252229 A1 Aug. 1, 2024

(30) Foreign Application Priority Data

Feb. 1, 2023 (GB) ...................................... 2301422

(51) Int. Cl.

*A61B 18/14* (2006.01)
*A61B 18/12* (2006.01)
*A61B 18/00* (2006.01)

(52) U.S. Cl.

CPC .......... *A61B 18/14* (2013.01); *A61B 18/1206* (2013.01); *A61B 2018/00452* (2013.01); *A61B 2018/1405* (2013.01); *A61B 2018/1467* (2013.01)

(58) Field of Classification Search

CPC .......... A61N 1/40; A61N 1/403; A61N 1/328; A61B 2018/00452–00476

See application file for complete search history.

(56) References Cited

U.S. PATENT DOCUMENTS

| | | | | |
|---|---|---|---|---|
| 5,052,997 | A | 10/1991 | Ruggera | |
| 5,101,836 | A | 4/1992 | Lee | |
| 8,321,031 | B1 | 11/2012 | Ellman et al. | |
| 2005/0065510 | A1 | 3/2005 | Carmel | |
| 2007/0106349 | A1 | 5/2007 | Karni | |
| 2008/0183167 | A1 | 7/2008 | Britva et al. | |
| 2008/0183252 | A1 | 7/2008 | Khen | |
| 2008/0312651 | A1* | 12/2008 | Pope | A61B 18/14 606/42 |

(Continued)

FOREIGN PATENT DOCUMENTS

| | | |
|---|---|---|
| EP | 1715810 | 5/2012 |
| WO | 20091126117 | 11/2012 |

OTHER PUBLICATIONS

Skin effect, Wikipedia, https://en.wikipedia.org/wiki/Skin_effect accessed Feb. 25, 2025 Skin Depth Equation Formula {aka Skin Effect)—RF Cafe, RF Cafe, https://www.rfcafe.com/references/electrical/skin-depth.htm accessed Feb. 25, 2025.

*Primary Examiner* — Sean W Collins
(74) *Attorney, Agent, or Firm* — The Law Office of Joseph L. Felber

(57) ABSTRACT

A system is disclosed for heating biological tissue via RF energy. The system comprises a source of RF energy at a frequency in excess of 25 Mhz and an applicator incorporating an electrode connected to the RF source for introducing RF energy into the biological tissue. The electrode comprises a hollow cylinder of which an end remote from the RF source defines an annular surface for contacting the biological tissue, the annular surface having an out diameter in excess of 3 cm.

16 Claims, 2 Drawing Sheets

(56) References Cited

U.S. PATENT DOCUMENTS

| | | | | |
|---|---|---|---|---|
| 2011/0009783 | A1 | 1/2011 | Dverin | |
| 2013/0245727 | A1 | 9/2013 | Kothare | |
| 2015/0045857 | A1* | 2/2015 | Britva | A61B 18/14 607/101 |
| 2017/0202606 | A1* | 7/2017 | Horton | A61B 18/1206 |

* cited by examiner

SYSTEM AND METHOD FOR HEATING BIOLOGICAL TISSUE

CROSS-REFERENCE TO RELATED APPLICATIONS

The present application gains priority from U.K. patent application no. GB 2301422.8 filed 1 Feb. 2023, which is incorporated by reference as if fully set-forth herein.

BACKGROUND OF THE INVENTION

The present invention relates to a system for heating biological tissue via RF energy.

The heating to which the present invention relates is for achieving a cosmetic improvement, not for the purpose of tissue ablation. EP 1715810 discloses a system for heating biological tissue which uses an electrode to apply RF energy to the tissue. The system described in the latter patent includes an applicator, forming a single electrode of the system, which comprises a dielectric barrier, contactable with a surface of a biological tissue to be heated. The applicator is capable of delivering a desired amount of energy to a predetermined energy dissipation zone beneath the surface of the biological tissue, the selected target being positioned within the predetermined energy dissipation zone. An RF energy source produces an output RF power signal directed to the single applicator, the RF being radiatively or capacitively coupled by the applicator into the biological tissue. A phase shifter is provided which is controllable to vary the phase of the output RF power signal so that energy from it is concentrated primarily in the predetermined energy dissipation zone, which lies at a phase dependent depth beneath the surface of the biological tissue. An impedance matching network serves to match the characteristic impedance of the biological tissue of the subject to that of the line from the RF source and the phase shifter, typically 50 Ohms, so that the RF power signal may pass through the surface of the biological tissue without undergoing reflection. An RF resonator is located in the applicator which is operative to accumulate and release the desired amount of energy cyclically whereby a significant portion of the energy of the RF signal is concentrated in the predetermined energy dissipation zone.

In operation, the applicator serves to convey the output RF power signal from the RF energy source through the surface of the biological tissue to the predetermined energy dissipation zone after the output has been processed by the phase shifter, the impedance matching network and the resonator. Operation of the system thereby produces a reverse thermal gradient in the biological tissue in that the surface is maintained at a lower temperature than the predetermined energy dissipation zone without needing to cool the surface.

The applicator does not connect a ground electrode to the biological tissue and therefore permits free propagation of the waves of the output RF power signal in the energy dissipation zone, without any distortion of electromagnetic field being produced by the ground.

RF radiation into biological tissue causes different heating effects at different frequencies. At frequencies around 2-15 MHz, the heating is predominantly resistive heating, resulting from the ionic conductivity of the biological tissue. At higher frequencies, such as a 25-50 MHz, the resistive heating reduces and the heating is instead caused predominantly by dielectric heating, resulting from rotation of water dipoles in the alternating fields.

Resistive heating suffers from the disadvantages of low penetration depth and inhomogeneous heat dissipation, which is dependent upon the conductivity of biological tissue and for this reason the present invention uses higher frequencies and relies on dielectric heating. However, the use of higher frequencies places a limit on the diameter of an electrode having a flat or spherical contact surface.

In practice, in order that a large area of tissue may be treated within an acceptable time, it is desirable for the energy dissipation zone to have a diameter of at least 4-6 cm. However, at higher frequencies, an electrode with a flat or dished surface of that diameter in contact with the biological tissue will result in uneven heating with the perimeter of the dissipation zone being heated to a greater extent than its centre. The higher frequencies therefore place a limit on the size of the applicator electrode, if an even heat distribution is to be achieved.

The present invention is predicated on the realisation that the limitation on the diameter of an electrode when using high frequency RF power, i.e. more that 25 MHz but preferably in the range of 40-50 MHz, is caused by the skin effect, The skin effect is the tendency for high frequency current to flow near the surface of an electrical conductor rather than uniformly through its entire cross section. High-frequency currents induce magnetic fields that in turn apply a force to the electrons in the high-frequency current itself that drives the moving electrons away from the centre of the current flow. In a wire, the current is pushed to the surface. The skin depth at a particular frequency, ω, is defined as the depth that includes 63% (1/e) of the total current flow and is given by the equation:

$$\delta = \sqrt{(2\rho/\omega\mu)}$$

where δ=skin depth, ρ=resistivity of the material, and u is the permeability of the material.

Therefore, in a solid applicator the RF-current is distributed in the manner shown schematically in FIG. 1 of the accompanying drawings, in which the current within the electrode is presented by the shaded area flowing in the direction indicated by the arrows The RF power coupled into the biological tissue is represented by arrows of which the length is indicative of its heating effect. The RF power reaches the contact surface at its periphery. At the periphery, some of the power is introduced into the biological tissue and the remaining reduced current flows towards the centre, The RF power coupled into the biological tissue thus reduces progressively as the current flows towards the centre of the electrode.

To address this problem, the present Applicant has previously proposed in U.S. Pat. No. 11,045,249 an electrode composed of a plurality of spaced pins.

SUMMARY OF THE INVENTION

The present invention provides, in accordance with a first aspect, a system for heating biological tissue via RF energy, the system comprising a source of RF energy at frequency in excess of 25 MHz and an applicator incorporating an electrode connected to the RF source for introducing the RF energy into the biological tissue, wherein the electrode comprises a hollow cylinder of which an end remote from the RF source defines an annular surface for contacting the biological tissue, the outer diameter of the annular surface exceeding 3 cm.

The term "annular" should not be construed herein as restricted to a region bounded by two concentric circles but more generally to a ring-like region that surrounds a central void, regardless of the shape of the inner and outer boundaries of the region. Hence, outline of the contact surface may for example be elliptical or polygonal. Also, if the inner and outer boundaries are circular, they need not be exactly concentric.

To increase the area of treatment further, in some embodiments, the system may comprise a plurality of concentric cylindrical electrodes each formed of a hollow cylinder of which an end remote from the RF source defines an annular surface for contacting the biological tissue, the electrodes being configured such that RF currents flow in parallel along all the cylindrical surfaces of the electrodes in the same direction as one another.

In accordance with a second aspect of the invention, there is provided a method of treatment of biological tissue which comprises applying RF energy at a frequency in excess of 25 MHz to the tissue using an electrode having at least one annular contact surface of which the outer diameter exceeds 3 cm and the radial dimension of the annular surface lies on the range of 5 mm to 6 mm.

In some embodiments, the electrode may comprise multiple annular contact surfaces arranged concentrically.

It should be noted that annular or cylindrical RF electrodes have been in used in the prior art to apply resistive heating for the purpose of tissue ablation. For example, US2005/0245800 discloses annular and concentric electrodes that operate at a frequency of less than 100 KHz, and have a diameter of no more that 3 mm. US2019/0142501 similarly discloses a surgical instrument for electrotomy that applies RF energy at a frequency below 4 MHz using electrodes no larger than a few millimetres in diameter. The prior art does not teach the use of cylindrical electrodes to achieve dielectric heating at a frequency in excess of 25 MHZ nor does it teach electrodes suitable for applying heat over an area exceeding 3 cm in diameter.

BRIEF DESCRIPTION OF DRAWINGS

The invention will now be described further, by way of example, with reference to the accompanying drawings, in which.

DETAILED DESCRIPTION OF THE INVENTION

A system of the present invention for heating biological tissue via RF energy may be the same as that disclosed in EP1715810, save for the design of the electrode that makes contact with the biological tissue to be treated. Thus, in addition to a generator of RF power, it may comprise a phase shifter, an impedance matching network and a resonator, all as disclosed in described in detail in EP 1715810.

Figure 1:
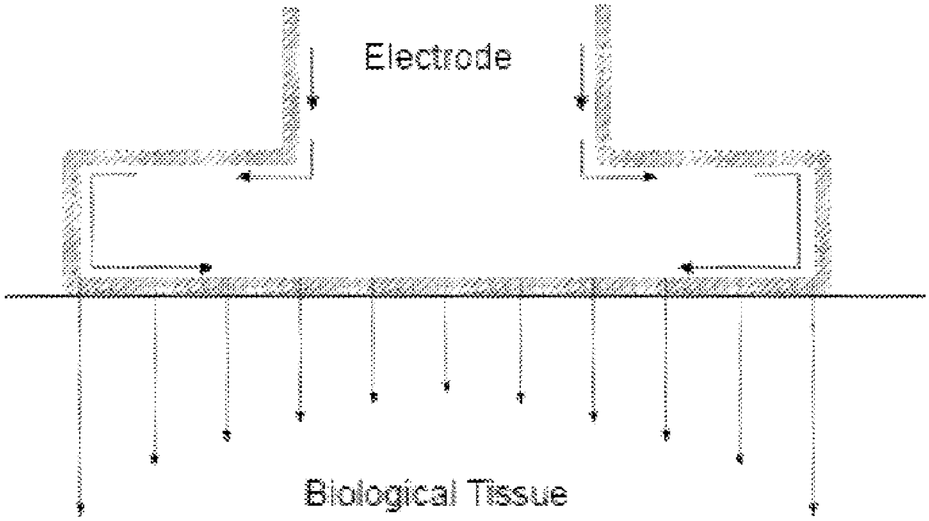
FIG. 1 shows schematically current flow at higher frequencies in a solid electrode and the resulting distribution of power coupled into biological surface in contact with the electrode.
Figure 2:
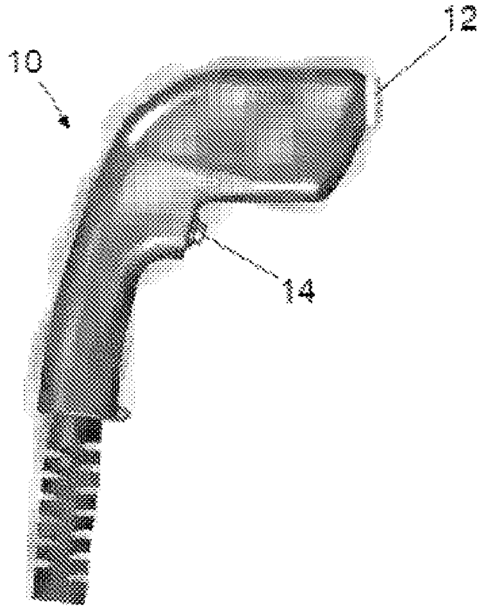
FIG. 2 is a side view of an applicator of a system of the invention.
Figure 3:
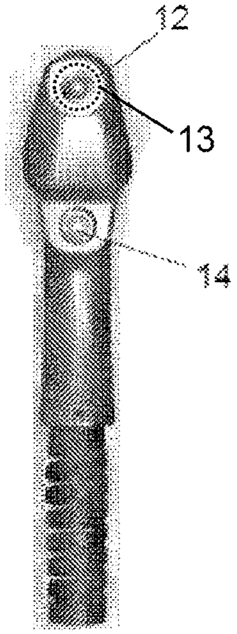
FIG. 3 is a front view of the applicator in FIG. 2.

As shown in FIGS. 2 and 3 of the accompanying drawings, the applicator 10 of a system of the invention has an electrode 12 that makes annular contact with the surface of the biological tissue to be treated and is defined by the annular flanged axial end surface of a hollow cylinder. The end flange sets the inner and outer rims of the contact area at the desired diameters without requiring the wall thickness of the cylindrical electrode to be increased. The outer diameter when applying a current at 40 to 50 MHz may typically be 3 cm to 5 cm and the radial thickness of the annular wall may be in the range of 5 mm to 6 mm. The annular end surface of the cylinder may be formed with indentations 13 to increase the area of contact with the biological tissue.

Figure 4:
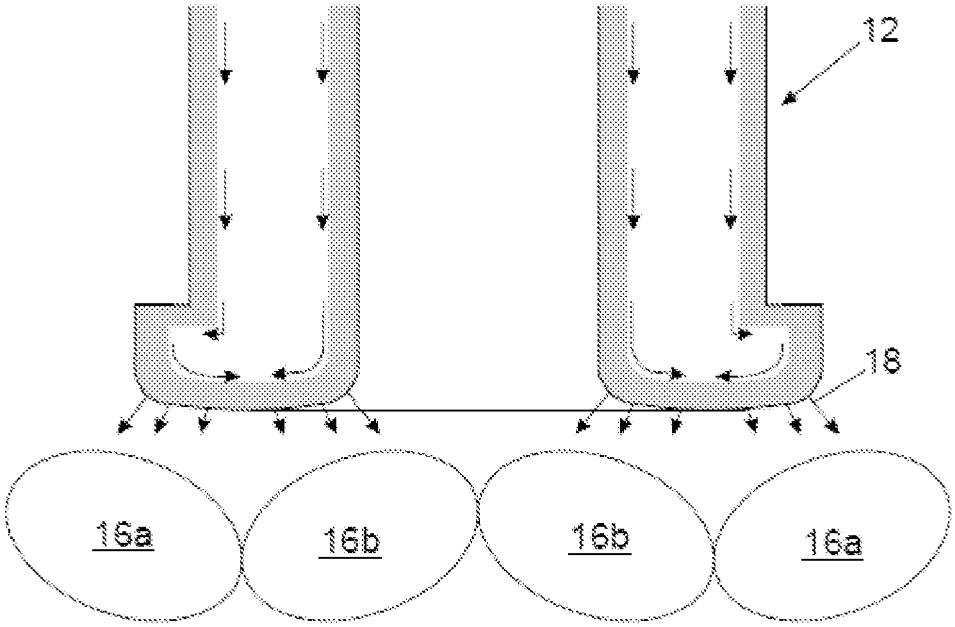
FIG. 4 is a schematic representation similar to that of FIG. 1 showing the distribution of power into a biological tissue when using an annular electrode.

As shown in FIG. 4, by a shaded area and arrows indicating the direction of flow, the current to the annular end surface flows along the outer and inner surfaces of the hollow cylindrical electrode 12. As a result, the current intensity at both the inner and the outer rim of the annular contact area is substantially the same. The current flowing into the biological tissue is as represented schematically the length of the arrow 18, that is to say that it is greatest at the inner and outer edges of the contact area and at its minimum at the mean diameter of the annular contract area.

The ellipses 16*a* in FIG. 4 represent schematically the annular hot zone created by the RF current flowing from the outer edge of the contact area and the ellipses 16*b* the annular hot zone recreated by the RF current flowing from the inner edge of the contact area. The centres of these ellipses represent the hottest part of each hot zone but their outline is not meant to represent zero heating but where the heating power falls to 50% of the maximum power. It will therefore be seen that the cumulative effect of the heating by the current flowing from the inner and outer rims of the electrode is substantially uniform over the entire area of the biological tissue lying beneath the electrode.

Figure 5:
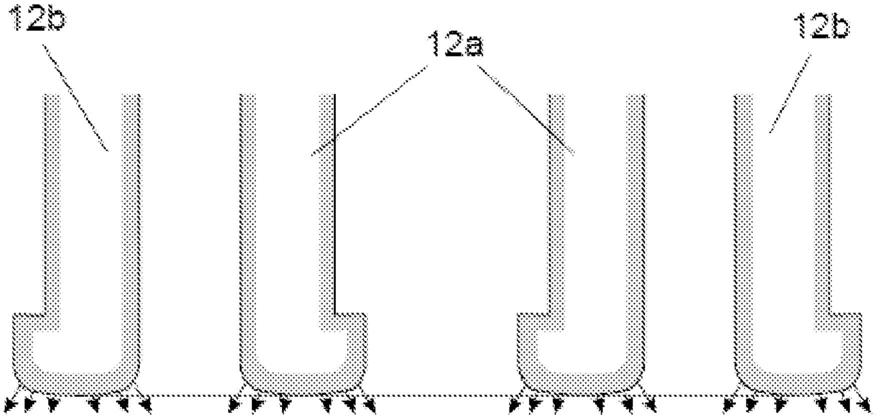
FIG. 5 is a representation similar to that of FIG. 4 of an embodiment having concentric annular electrodes.

It will be appreciated that to create a still larger treatment area, it would be possible to provide, as shown in FIG. 5, one (or more) cylindrical electrode(s), in which an inner electrode 12*a* is surrounded by an electrode 12*b*. In such an embodiment, it is important the currents flowing to each rim of each annular contact surface are substantially independent of one another. By this, it is meant that an increase in the magnitude of any one current should not result in any change in the magnitude of the other currents. This is achieved if the currents flow in parallel along a respective cylindrical surface and in the same direction as one another.

The invention claimed is:

1. A system for heating biological tissue via RF energy, the system comprising a source of RF energy at frequency in excess of 25 MHz and an applicator incorporating an electrode connected to the RF source for introducing the RF energy into the biological tissue, wherein the electrode comprises a hollow cylinder of which an end remote from the RF source defines an annular surface that surrounds a central void for contacting the biological tissue, the outer diameter of the annular surface exceeding 3 cm, so that when said annular surface contacts the biological tissue and said source of RF energy is activated, the biological tissue is heated by dipole heating.

2. A system as claimed in claim 1, wherein the system comprises a plurality of concentric cylindrical electrodes each formed of a hollow cylinder of which an end remote from the RF source defines an annular surface for contacting the biological tissue, and wherein the electrodes are configured such that RF currents flow in parallel along all the cylindrical surfaces of the electrodes in the same direction as one another.

3. A system as claimed in claim 1, wherein the wall thickness of the cylindrical electrode is 5 mm to 6 mm.

4. A system as claimed in claim 1, wherein said annular surface is formed with indentations increasing the surface area of said annular surface, thereby increasing the area of biological tissue which said annular surface contacts.

5. The system of claim 1, wherein said source of RF energy is at a frequency of 40-50 MHz.

6. The system of claim 1, comprising either:

a single said electrode so that there is a single said annular surface for contacting biological tissue; or two said electrodes arranged one inside the other so that there are two said annular surfaces for contacting biological tissue, said annular surfaces arranged concentrically.

7. The system of claim 1, wherein said electrode comprises an annular flanged axial end surface of the hollow cylinder.

8. The system of claim 1, wherein a ground electrode is absent.

9. A method of treatment of biological tissue which comprises applying RF energy at a frequency in excess of 25 MHz to the tissue using an electrode having at least one annular contact surface of which the outer diameter exceeds 3 cm that surrounds a central void and the radial dimension of the annular surface is 5 mm to 6 mm, so that when said annular surface contacts the biological tissue and said source of RF energy is activated, the biological tissue is heated by dipole heating.

10. A method as claimed in claim 9, wherein the electrode comprises multiple annular contact surfaces arranged concentrically.

11. The method of claim 9, wherein said source RF energy is at a frequency of 40-50 MHz.

12. The method of claim 9, comprising either:

a single said electrode so that there is a single said annular surface for contacting biological tissue; or two said electrodes arranged one inside the other so that there are two said annular surfaces for contacting biological tissue, said annular surfaces arranged concentrically.

13. The method of claim 9, said electrode comprising multiple annular contact surfaces arranged concentrically.

14. The method of claim 9, wherein said electrode comprises an annular flanged axial end surface of the hollow cylinder.

15. The method of claim 9, wherein said annular end surface is formed with indentations increasing the surface area of said annular surface, thereby increasing the area of biological tissue which said annular surface contacts.

16. The method of claim 9, wherein a ground electrode is absent.

* * * * *